(12) United States Patent
Bonrath et al.

(10) Patent No.: US 7,803,952 B2
(45) Date of Patent: Sep. 28, 2010

(54) MANUFACTURE OF LACTONES

(75) Inventors: Werner Bonrath, Freiburg (DE); Reinhard Karge, Staufen (DE); Felix Roessler, Kaiseraugst (CH)

(73) Assignee: DSM IP Assets B.V., Heerlen (NL)

( * ) Notice: Subject to any disclaimer, the term of this patent is extended or adjusted under 35 U.S.C. 154(b) by 121 days.

(21) Appl. No.: 11/886,780

(22) PCT Filed: Apr. 7, 2006

(86) PCT No.: PCT/EP2006/003163

§ 371 (c)(1), (2), (4) Date: Mar. 24, 2008

(87) PCT Pub. No.: WO2006/108562

PCT Pub. Date: Oct. 19, 2006

(65) Prior Publication Data

US 2009/0043106 A1    Feb. 12, 2009

(30) Foreign Application Priority Data

Apr. 8, 2005   (EP) .................................. 05007722

(51) Int. Cl.
*C07D 491/048*   (2006.01)

(52) U.S. Cl. .................................................. 548/303.1
(58) Field of Classification Search ............. 548/303.1; 549/313, 321

See application file for complete search history.

(56) References Cited

FOREIGN PATENT DOCUMENTS

WO    WO 2004/094367    11/2004

OTHER PUBLICATIONS

Matsuki et al, "Enantioselective Reduction of *meso*-Cyclic-1,2-dicarboxylic anhydrides and 1,2-Dicarboximides: Asymmetric Synthesis of Bicyclic Lactones and Hydroxylactams", Chemical and Pharmaceutical Bulletin Pharmaceutical Society of Japan, Tokyo, JP, vol. 42, No. 1, Jan. 1994.

Okada et al, "catalytic Asymmetric Hydrogenation of Cyclic Anhydrides Using Ruthenium(II) Chiral Phosphine Complex", Tetrahedron Letters, vol. 22, No. 43, 1981, pp. 4297-4300.

International Search Report mailed Aug. 3, 2006 in PCT/EP2006/003163.

Written Opinion mailed Aug. 3, 2006 in PCT/EP2006/003163.

*Primary Examiner*—Kamal A Saeed
*Assistant Examiner*—Kristin Bianchi
(74) *Attorney, Agent, or Firm*—Nixon & Vanderhye P.C.

(57) ABSTRACT

The present invention relates to a process for the manufacture of cyclic monocarboxylic esters (lactones) and related compounds by hydrogenation of cyclic dicarboxylic acid anhydrides in the presence of metal catalysts.

22 Claims, No Drawings

MANUFACTURE OF LACTONES

This application is the US national phase of international application PCT/EP2006/003163 filed 7 Apr. 2006 which designated the U.S. and claims benefit of EP 05007722.1, dated 8 Apr. 2005, the entire content of which is hereby incorporated by reference.

The present invention relates to a process for the manufacture of cyclic monocarboxylic esters (lactones) and related compounds by hydrogenation of cyclic dicarboxylic acid anhydrides in the presence of metal catalysts. The products of this process are useful as pharmaceutical or vitamin-type active substances, or as intermediates for they manufacture of such active substances.

By the application of the inventive process, in which the starting materials may be prochiral cyclic dicarboxylic acid anhydrides, the so manufactured lactones have been found to feature surprisingly high chemo- and enantioselectivities and to be obtained in surprising high chemical and optical yields.

Selective hydrogenations of anhydrides are not widely known. Osakada et al. disclose in Tetrahedron Letters, Vol. 22, No. 43, pp 4297-4300 (1981) a catalytic asymmetric hydrogenation of cyclic anhydrides using ruthenium(II) chiral phosphine complexes, wherein the substrates are carbon substituted bicyclic anhydrides.

The invention relates to a process for the manufacture of a lactone of the general formula

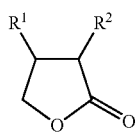

I or a hydroxylactone of the general formula

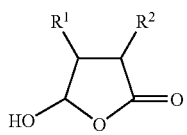

I' or the ring-opened hydroxylactone of the general formula

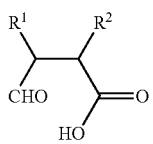

I'' wherein each of $R^1$ and $R^2$, independently, signifies $-NR^4R^5$ and $R^4$ and $R^5$, each independently, signify hydrogen, substituted or unsubstituted alkyl, substituted or unsubstituted alkenyl, substituted or unsubstituted cycloalkyl, substituted or unsubstituted aryl, optionally aromatically substituted arylalkyl, optionally aromatically substituted arylalkenyl, cycloalkylalkyl substituted or unsubstituted on the cycloalkyl moiety, heterocyclyl, substituted or unsubstituted alkanoyl, substituted or unsubstituted aroyl, substituted or unsubstituted alkylsulphonyl, substituted or unsubstituted arylsulphonyl or a silyl group $Si(allyl)_3$, $Si(aryl)_3$ or $Si(alkyl)_{1\ or\ 2}(aryl)_{2\ or\ 1}$, or the two symbols $R^4$ alternatively form together a carbonyl group and the two remaining symbols $R^5$, each independently, have one of the above-mentioned significances stated for $R^4$ and $R^5$, characterized by hydrogenating a cyclic dicarboxylic acid anhydride of the general formula

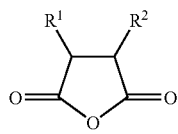

II wherein $R^1$ and $R^2$ have the significances given above, in the presence of a group VIII metal catalyst.

In the above definition of the various significances for $R^3$, $R^4$ and $R^5$ any alkyl embraces straight-chain or (in the case of 3 or more carbon atoms) branched alkyl groups, preferably with up to 12 carbon atoms, more preferably with up to 6 carbon atoms, such as methyl, ethyl, isopropyl, tert. butyl, neopentyl and n-hexyl. This applies equally to the alkyl part of such substituted or unsubstituted groups as the arylalkyl, cycloalkylalkyl, alkanoyl and alkylsulphonyl groups and to alkyl of the silyl group $Si(alkyl)_3$ or $Si(alkyl)_{1\ or\ 2}(aryl)_{2\ or\ 1}$. Any alkenyl, as such or as part of an substituted or unsubstituted arylalkenyl group, embraces straight-chain or branched alkenyl groups, suitably with up to 12 carbon atoms, more preferably up to 6 carbon atoms, featuring and depending on the number of carbon atoms up to three double bonds, preferably one double bond. An example of an alkenyl group is allyl. Any cycloalkyl, as such or as part of an substituted or unsubstituted cycloalkylalkyl group, suitably contains from 3 to 8 carbon atoms, preferably from 4 to 7 carbon atoms. Any aryl, as such or as part of an substituted or unsubstituted arylalkyl, arylalkenyl, aroyl or arylsulphonyl group, and of the silyl group $Si(aryl)_3$ or $Si(alkyl)_{1\ or\ 2}(aryl)_{2\ or\ 1}$, is suitably phenyl, 1-naphthyl or 2-naphthyl, preferably phenyl. Any heterocyclyl may be such a group of at least partially saturated nature or of aromatic (heteroaromatic) nature and featuring as ring heteroatoms at least one selected from oxygen, sulphur and nitrogen atoms, whereby two or more of such atoms in the ring may be the same or different heteroatoms. Examples of such groups are tetrahydrofuranyl, tetrahydrodioxanyl, tetrahydrothiophenyl, pyrrolidinyl, piperidinyl, morpholinyl, piperazinyl, dihydrofuranyl, dihydrodioxanyl, dihydrothiophenyl, pyrrolyl and pyridyl, and any such groups able to feature one or more fused benzene rings and/or bear a substituent, particularly an alkyl group, on a secondary ring nitrogen atom.

Suitable substituents for substituted or unsubstituted alkyl, alkenyl, alkanoyl or alkylsulphonyl include one or more substituents selected from $C_{1-4}$-alkoxy and $C_{1-4}$-alkylthio, whereby two or more substituents on the same alkyl or alkenyl may be the same or different. In the case of alkoxyalkyl, this is preferably alkoxymethyl optionally bearing one or two alkyl substituents on the methylene moiety. Suitable substituents for substituted or unsubstituted cycloalkyl include one or more, same or different, $C_{1-4}$-alkyl. Suitable substituents for substituted or unsubstituted aryl include are $C_{1-4}$-alkyl and $C_{1-4}$-alkoxy, whereby in this case, too, two or more substituents may be the same or different. This information on the kinds of substituents which come into question equally applies to the cycloalkyl and aryl moieties when part of optionally aromatically substituted arylalkyl, optionally aromatically substituted arylalkenyl, substituted or unsubstituted cycloalkylalkyl, substituted or unsubstituted aroyl and substituted or unsubstituted arylsulphonyl, as appropriate.

In the employed group VIII metal catalyst the group VIII metal (iron, cobalt, nickel, ruthenium, rhodium, palladium, osmium, iridium or platinum) is especially ruthenium (Ru), rhodium (Rh) or iridium (Ir). The catalyst can be homogeneous or heterogeneous, chiral or achiral.

The metal catalyst can be the metal itself, the metal together with a chiral and/or achiral modifier, or a metal complex in which the metal has formally a zero or positive oxidation state. The metal complex can be free or immobilized on a suitable support, such as active carbon, an organic polymer, an inorganic or organic ion exchanger or an inorganic material, e.g. silica, titania or alumina. The modifier in the case of the metal itself, and the complexing molecule in the case of the metal complex catalyst, can be a mono-, bi- or multidentate compound featuring one or more phosphorus, nitrogen, oxygen and/or sulphur atoms which act as the linking sites to the metal atom.

Furthermore, additional organic compounds with metal-complexing properties and featuring one or more phosphorus, nitrogen and/or sulphur atoms and/or functional groups which can coordinate with the metal may be present as a part of the catalytic system or an integral part of the catalytic system. Suitable functional groups include double bonds as occurring in olefins with one or more double bonds and in aromatic compounds.

Further constituents of the catalytic system may be inorganic and/or organic salts and/or protonic acids.

Suitable homogeneous metal complex catalysts are for example of the formula III or IV:

[A$_1$MeYZ]     III

[A$_1$MeY]$^+$E$_1^-$     IV wherein A$_1$ signifies two tertiary monophosphine ligands or a ditertiary diphosphine ligand, which together with the metal atom (Me) forms a 5- to 10-membered, preferably 5- to 8-membered, especially a 5- to 7-membered ring, Me signifies noble metal, especially Rh, Ru or Ir, Y signifies two olefines or a diene, Z signifies Cl, Br or I, and E$_1^-$ signifies the anion of a protonic or complex acid Suitable olefins Y include a $C_{2-12}$-, preferably a $C_{2-6}$- and especially a $C_{2-4}$-olefine, such as propene, 1-butene and (most preferably) ethylene. The diene, being the alternative significance of Y, can contain 5-12, preferably 5-8, carbon atoms, and can be aliphatic, cyclic or polycyclic. The two double bonds in the diene are preferably separated by a single or two methylene groups. Examples are 1,3-pentadiene, cyclopentadiene, 1,5-hexadiene, 1,4-cyclohexadiene, 1, 4 or 1,5-heptadiene, 1,4- or 1,5-cycloheptadiene, 1,4- or 1,5-octadiene, 1,4- or 1,5-cyclooctadiene and norbornadiene. Preferably, Y signifies two ethylene or 1,5-hexadiene, 1,5-cyclooctadiene or norbornadiene.

Z in the formula III is preferably Cl or Br. Examples of E$_1^-$ in the formula IV are ClO$_4^-$, CF$_3$SO$_3^-$, CH$_3$SO$_3^-$, HSO$_4^-$ BF$_4^-$, B(phenyl)$_4^-$, B(3,5-di(trifluoromethyl)-phenyl)$_4^-$, PF$_6^-$, SbCl$_6^-$, AsF$_6^-$ and SbF$_6^-$.

The tertiary monophosphine ligands, being one of the two significances for A$_1$ in both formulae III and IV, feature bound to one phosphorus atom three oxygen-bound substituents (phosphites), two oxygen-bound substituents and a nitrogen-bound substituent or three carbon-bound substituents. The alternative (single) ditertiary diphosphine ligand is one wherein two phosphorus atoms are linked by a bridging group and the phosphorous atoms are bound to the bridging group via oxygen, nitrogen or carbon atoms, and wherein the phosphorus atoms bear two oxygen- or carbon-bound substituents.

Two oxygen-bound substituents preferably form the residue of a diol, so that a cyclic phosphonite group is present. The diols are preferably 2,2'-dihydroxy-1,1'-diphenyls or -binaphthyls, which can be mono- or multiply substituted, especially at the 6- and/or 6'-positions for example with $C_{1-8}$-alkyl, $C_{5-8}$-cycloalkyl, $C_{5-8}$-cycloalkyl-$C_{1-4}$-alkyl, $C_{6-10}$-aryl, $C_{7-12}$-aralkyl, $C_{1-8}$-alkoxy, $C_{5-8}$-cycloalkyloxy, $C_{5-8}$-cycloalkyl-$C_{1-4}$-alkoxy, $C_{6-10}$-aryloxy or $C_{7-12}$-aralkyloxy. Examples are methyl, ethyl, propyl, butyl, cyclohexyl, cyclohexylmethyl, phenyl, benzyl, methoxy, ethoxy, propoxy, butoxy, cyclohexyloxy, phenyloxy and benzyloxy.

Tertiary monophosphines and ditertiary diphosphines are well known in numerous examples and described in the literature. Monophosphines and diphosphines can be chiral, thus promoting the formation of optical isomers to a large extent when prochiral cyclic dicarboxylic acid anhydrides are hydrogenated in accordance with the process of the present invention.

Suitable tertiary monophosphines with three oxygen-bound or two oxygen-bound and a nitrogen-bound substituents are of the formulae V and VI

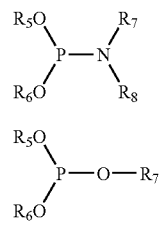

wherein R$_5$, R$_6$, R$_7$ and R$_8$, independently, signify a monovalent, unsubstituted or substituted aliphatic, heteroaliphatic, cycloaliphatic, heterocycloaliphatic, cycloaliphatic-aliphatic, heterocycloaliphatic-aliphatic, aromatic, heteroaromatic, aromatic-aliphatic or heteroaromatic-aliphatic groups, R$_5$ and R$_6$ together form a bivalent, unsubstituted or substituted aliphatic, heteroaliphatic, cycloaliphatic, heterocycloaliphatic, cycloaliphatic-aliphatic-, heterocycloaliphatic-aliphatic, aromatic, heteroaromatic, aromatic-aliphatic or heteroaromatic-aliphatic group, and R$_7$ and R$_8$ together with the nitrogen atom form a 5- or 6-membered ring.

R$_5$ and R$_6$ together preferably form a bivalent group, especially unsubstituted or substituted 1,1'-binaphth-2,2'-diyl or 1,1'-biphen-2,2'-diyl. Examples of the latter are ligands of the formulae

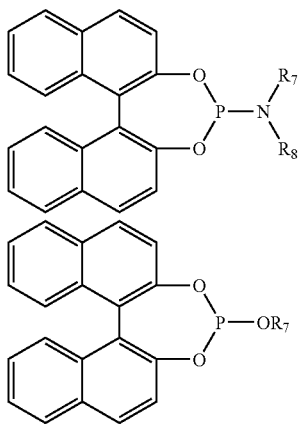

wherein $R_7$ and $R_8$ have the significances given above.

Suitable tertiary monophosphines include three C-bound substituents selected from unsubstituted or substituted aliphatic, heteroaliphatic, cycloaliphatic, heterocycloaliphatic, cycloaliphatic-aliphatic, heterocycloaliphatic-aliphatic, aromatic, heteroaromatic, aromatic-aliphatic and heteroaromatic-aliphatic groups, which suitably contain up to 18, preferably up to 12, and especially up to 8 carbon and/or heteroatoms, and 4 to 8, preferably 5 to 7, especially 5 or 6 ring members. The cyclic groups can be linked, fused or fused and linked to polycyclic groups, and such ring systems can contain for example 2 to 6, preferably 2 to 4, cyclic or heterocyclic carbon atoms.

Heteroatoms or groupings in heterocyclic groups can be selected from —O—, —S—, =N—, —HN— or —$R_a$N— wherein $R_a$ preferably signifies $C_{1-8}$-alkyl, $C_{5-8}$-cycloalkyl, $C_{5-8}$-cycloalkyl-$C_{1-4}$-alkyl, $C_{6-10}$-aryl, $C_{7-12}$-aralkyl or $C_{1-8}$-acyl, The aliphatic or heteroaliphatic groups can be for example straight-chain or branched $C_{1-12}$-alkyl, preferably $C_{3-8}$-alkyl, which optionally feature one or more interpolated oxygen and/or sulphur atoms (and thus are for example alkoxyalkyl, alkoxyalkoxyalkyl, alkylthioalkyl, alkylthioalkylthioalkyl etc. groups or analogous groups featuring both oxygen and thio chain members). The cycloaliphatic groups are suitably $C_{5-8}$-cycloalkyl, and the heterocycloaliphatic groups are suitably cyclic groups with 5 to 8 ring members including carbon atoms and, as heteroatoms or groupings, one or more —O—, —S— and/or —$NR_a$— ($R_a$ as given above). The cycloaliphatic-aliphatic groups are suitably $C_{5-8}$-cycloalkyl-$C_{1-4}$-alkyl, and the heterocycloaliphatic-aliphatic groups feature the heterocycloaliphatic part of the group as explained above for "heterocycloaliphatic", and the alkyl part with 1 to 4 carbon atoms. The aromatic and heteroaromatic groups are suitably $C_{6-12}$-aryl and, respectively, $C_{5-11}$-heteroaryl featuring one or more heteroatoms or groupings selected from —O—, —S—, =N—, —HN— and —$R_a$N— ($R_a$ as given above). In the aromatic-aliphatic or heteroaromatic-aliphatic groups, which are suitably $C_{6-12}$-aryl-$C_{1-4}$-alkyl or, respectively, $C_{5-11}$-heteroaryl-$C_{1-4}$-alkyl, the $C_{5-11}$-heteroalkyl part of the latter group is as explained above for "$C_{5-11}$-heteroaryl".

The tertiary monophosphines can also be P-substituted P-cyclic rings with for example altogether 4-6 ring members (phosphetanes, phospholanes and phosphanes). The P-substituents can be substituted, for example as later explained for the ditertiary diphosphines. Examples of the monophosphines are trimethylphosphine, tri-tert. butylphosphine, tri-hexylphosphine, tricyclohexylphosphine, trinorbornylphosphine, triadamantylphosphine, triphenylphosphine, tritoluoylphosphine, trixylylphosphine, phenylphospholane and diphenyl-tert. butylphosphine.

The achiral and chiral ditertiary diphosphines include those in which both phosphine groups are bound to straight-chain or cyclic linking hydrocarbon groups at different positions, preferably (a) to different carbon atoms of a $C_{2-6}$-carbon chain, said chain being part of a monocyclic ring or part of a bicyclic ring system, as for example biphenyl or binaphthyl, or cyclopentadienyl-phenyl, cyclopentadienyl-$CH_2$-phenyl or cyclopentadienyl-CH(OCH$_3$)-phenyl in ferrocenes, or (b) to in each case a cyclopentadienyl ring of an substituted or unsubstituted ferrocene.

The ditertiary of diphosphine ligands contain two secondary phosphine groups $X_1$ and $X_2$, which can contain two identical or different hydrocarbon groups, preferably two identical hydrocarbon groups. Moreover, the secondary phosphine groups $X_1$ and $X_2$ can be the same or different.

The hydrocarbon groups can be unsubstituted or substituted and/or contain heteroatoms selected from O, S or N. They can contain 1 to 22, preferably 1 to 12, and especially 1 to 8 carbon atoms. A preferred secondary phosphine is one wherein the phosphine group contains two same or different groups selected from straight-chain or branched $C_{1-12}$-alkyl; unsubstituted $C_{5-12}$-cycloalkyl or $C_{5-12}$-cycloalkylmethyl or this groups substituted with $C_{1-6}$-alkyl or $C_{1-6}$-alkoxy; phenyl, naphthyl, furyl or benzyl; or phenyl or benzyl substituted (in the case of benzyl, on the aromatic ring) with halogen (particularly F, Cl or Br), $C_{1-6}$-alkyl, $C_{1-6}$-haloalkyl (e.g. trifluoromethyl), $C_{1-6}$-alkoxy, $C_{1-6}$-haloalkoxy (e.g. trifluoromethoxy), $(C_6H_5)_3Si$, $(C_{1-12}$-alkyl$)_3Si$, dialkylamino or —$CO_2$—$C_{1-6}$-alkyl (e.g. —$CO_2CH_3$).

Examples of the P-substituents being alkyl, which preferably contains 1 to 6 carbon atoms, are methyl, ethyl, n-propyl, isopropyl, n-butyl, isobutyl, tert. butyl and the isomers of pentyl and hexyl. Examples of the P-substituents being optionally alkyl substituted cycloalkyl are cyclopentyl, cyclohexyl, methyl- and ethylcyclohexyl, and dimethylcyclohexyl. Examples of P-substitutents being alkyl, alkoxy, haloalkyl, haloalkoxy and halogen substituted phenyl and benzyl are o-, m- and p-fluorophenyl, o-, m- and p-chlorophenyl, difluoro- and dichlorophenyl, pentafluorophenyl, methylphenyl, dimethylphenyl, trimethylphenyl, ethylphenyl, methylbenzyl, methoxyphenyl, dimethoxyphenyl, trifluoromethylphenyl, bis-trifluoromethylphenyl, tris-trifluoromethylphenyl, trifluoromethoxyphenyl, bis-trifluoromethoxyphenyl and 3,5-dimethyl-4-methoxyphenyl.

Preferred secondary phosphine groups are those which feature identical groups selected from $C_{1-6}$-alkyl; unsubstituted cyclopentyl or cyclohexyl; cyclopentyl or cyclohexyl substituted with 1 to 3 $C_{1-4}$-alkyl and/or $C_{1-4}$-alkoxy groups; and phenyl and benzyl, each unsubstituted or substituted (in the case of benzyl, aromatically) with 1 to 3 $C_{1-4}$-alkyl, $C_{1-4}$-alkoxy, fluorine, chlorine, $C_{1-4}$-fluoroalkyl and/or $C_{1-4}$-fluoroalkoxy (up to 3 of the same or different substituents).

The secondary phosphino group preferably has the formula —$PR^9R^{10}$, wherein each of $R^9$ and $R^{10}$, independently of one another, signifies a hydrocarbon group with 1 to 18 carbon atoms and which is unsubstituted or substituted with halogen, $C_{1-6}$-alkyl, $C_{1-6}$-haloalkyl, $C_{1-6}$-alkoxy, $C_{1-6}$-haloalkoxy, $(C_{1-4}$-alkyl$)_2$amino, $(C_6H_5)_3Si$, $(C_{1-12}$-alkyl$)_3Si$ or —$CO_2$—$C_{1-6}$-alkyl, and/or heteroatoms O.

Preferably, $R^9$ and $R^{10}$ are the same groups selected from straight-chain or branched $C_{1-6}$-alkyl, unsubstituted cyclopentyl or cyclohexyl; cyclopentyl or cyclohexyl substituted with 1 to 3 $C_{1-4}$-alkyl and/or $C_{1-4}$-alkoxy groups; furyl; unsubstituted benzyl; benzyl substituted aromatically with 1 to 3 $C_{1-4}$-alkyl and/or $C_{1-4}$-alkoxy groups; or, especially, unsubstituted phenyl or phenyl substituted with 1 to 3 groups/atoms selected from the same or different $C_{1-4}$-alkyl, $C_{1-4}$-alkoxy, amino, di($C_{1-6}$-alkyl)amino, hydroxyl, fluorine, chlorine, $C_{1-4}$-fluoroalkyl and $C_{1-4}$-fluoroalkoxy. $R^9$ and $R^{10}$ most preferably signify identical groups selected from $C_{1-6}$-alkyl, cyclopentyl, cyclohexyl, furyl or substituted or unsubstituted phenyl, the optionally present substituents being up to three $C_{1-4}$-alkyl, $C_{1-4}$-alkoxy and $C_{1-4}$-fluoroalkyl groups, and, where two or three of such substituents are present, these being the same or different.

The secondary phosphine groups $X_1$ and $X_2$ can be cyclic secondary phosphino, e.g. with substituted or unsubstituted ring structures

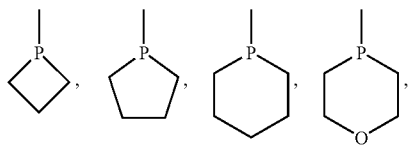

the optionally present substituents being one or more groups selected from hydroxyl, $C_{1-8}$-alkyl, $C_{4-8}$-cycloalkyl, $C_{1-6}$-alkoxy, $C_{1-4}$-alkoxy-$C_{1-4}$-alkyl, phenyl, $C_{1-4}$-alkyl- or $C_{1-4}$-alkoxyphenyl, benzyl $C_{1-4}$-alkyl- or $C_{1-4}$-alkoxybenzyl, benzyloxy, $C_{1-4}$-alkyl- or $C_{1-4}$-alkoxybenzyloxy, and $C_{1-4}$-alkylidene-dioxy.

The substituents can be present in one or both the α-positions to the phosphorus atom to enable the presence of chiral carbon atoms. Preferably, the substituents in one or both to the α-positions are $C_{1-4}$-alkyl, e.g. methyl, ethyl, n- or iso-propyl; $C_{1-4}$-alkoxymethyl; benzyl; or $C_{6-10}$-aryloxymethyl.

The optionally present substituents an alternatively be present in the two positions β and γ to the phosphorus atom, and in this case the substituents may include divalent substituents attached at the β- and γ-positions. Examples of substituents for β- and/or γ-positions are $C_{1-4}$-alkyl, $C_{1-4}$alkoxy, benzyloxy and (divalent substituents) —O—CH$_2$—O—, —O—CH($C_{1-4}$-alkyl)-O— and —O—C($C_{1-4}$-alkyl)$_2$-O—. Preferred such substituents are methyl, ethyl, methoxy, ethoxy, —O—CH(methyl)-O—, and —O—C(methyl)$_2$-O—.

Further known and suitable phosphine groups are those derived from cyclic and chiral phospholanes with 7 carbon atoms in the ring, e.g. those of the formulae

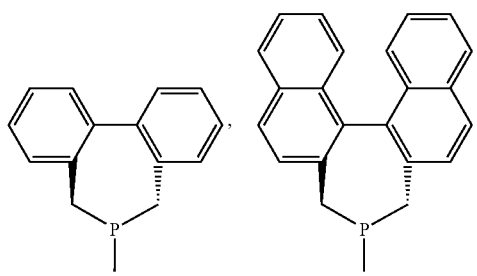

in which the aromatic rings can feature one or more substituents selected from $C_{1-4}$-alkyl, $C_{1-4}$-alkoxy, $C_{1-4}$-alkoxy-$C_{1-2}$-alkyl, phenyl, benzyl, benzyloxy and $C_{1-4}$-alkylidene-dioxy and $C_{1-4}$-alkylene-dioxy. Information on such cyclic and chiral phospholanes is known from such publications as US 2003/0073868 A1 and WO 02/048161.

Depending on the types, positions and the number of substituents the cyclic phosphine groups can be C-chiral, P-chiral or C- and P-chiral.

The cyclic secondary phosphino groups can for example conform to the following formulae, in each of which only one of the possible diastereoisomers is represented:

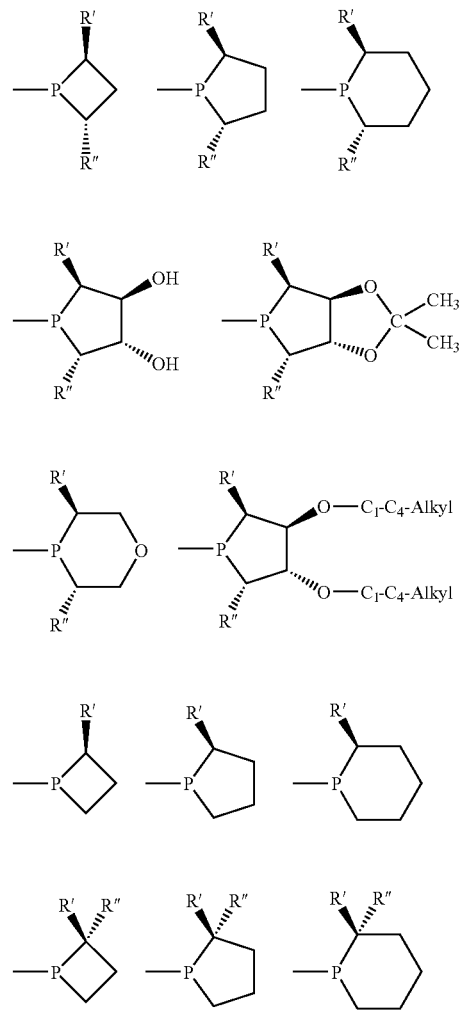

wherein R' or each of R' and R", independently, signifies/signify $C_{1-4}$-alkyl, e.g. methyl, ethyl, n- or isopropyl; $C_{1-4}$-alkoxymethyl; benzyl; or $C_{6-10}$-aryloxymethyl. Additionally, in these cases where R' and R" are bound to the same carbon atom, they can together form $C_4$- or $C_5$-alkylene.

In a preferred embodiment, $X_1$ and $X_2$ signify the same or different non-cyclic secondary phosphine group(s) selected from —P($C_{1-6}$-alkyl)$_2$, —P($C_{5-8}$-cycloalkyl)$_2$, —P($C_{7-8}$-bicycloalkyl)$_2$, —P(o-furyl)$_2$, —P($C_6H_5$)$_2$, —P[2-($C_{1-6}$-alkyl)-$C_6H_4$]$_2$, —P[3-($C_{1-6}$-alkyl)-$C_6H_4$]$_2$, —P[4-($C_{1-6}$-alkyl)-$C_6H_4$]$_2$, —P[2-($C_{1-6}$-alkoxy)-$C_6H_4$-($C_{1-6}$-alkoxy)-$C_6H_4$]$_2$, —P[2-trifluoromethyl-$C_6H_4$]$_2$, —P[3-trifluoromethyl-$C_6H_4$]$_2$, —P[4-trifluoromethyl-$C_6H_4$]$_2$, —P[3,5-di(trifluoromethyl)-$C_6H_3$]$_2$, —P[3,5-di($C_{1-6}$-alkyl)-$C_6H_3$]$_2$, —P[3,5- di($C_{1-6}$-alkoxy)-$C_6H_3$]$_2$ and —P[3,5-di($C_{1-6}$-alkyl)-4-($C_{1-6}$-alkoxy)-$C_6H_2$]$_2$, or a cyclic secondary phosphine group of one of the formulae

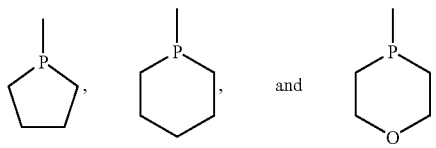

which in each case is unsubstituted or mono- or multiply substituted with $C_{1-4}$-alkyl, $C_{1-4}$-alkoxy, $C_{1-4}$-alkoxy-$C_{1-2}$-alkyl, phenyl, benzyl, benzyloxy or $C_{1-4}$-alkylidene-dioxy.

Some specific examples of the non-cyclic and cyclic secondary phosphine groups are —P(CH$_3$)$_2$, —P(isoC$_3$H$_7$)$_2$, P(n-C$_4$H$_9$)$_2$, —P(isoC$_4$H$_9$)$_2$, —P(C$_6$H$_{11}$)$_2$, —P(norbornyl)$_2$, —P(o-furyl)$_2$, —P(C$_6$H$_5$)$_2$, P[2-methyl-C$_6$H$_4$]$_2$, P[3-methyl-C$_6$H$_4$]$_2$, —P[4-methyl-C$_6$H$_4$]$_2$, —P[2-methoxy-C$_6$H$_4$]$_2$, —P[3-methoxy-C$_6$H$_4$]$_2$, —P[4-methoxy-C$_6$H$_4$]$_2$, —P[3-trifluoromethyl-C$_6$H$_4$]$_2$, —P[4-trifluoromethyl-C$_6$H$_4$]$_2$, —P[3,5-di(trifluoromethyl)-C$_6$H$_3$]$_2$, —P[3,5-dimethyl-C$_6$H$_3$]$_2$, —P[3,5-dimethoxy-C$_6$H$_3$]$_2$, and —P[3,5-dimethyl-4-methoxy-C$_6$H$_2$]$_2$, and those groups of the formulae wherein R' and R" have the same significances and are each methyl, ethyl, methoxy, ethoxy, phenoxy, benzyloxy, methoxymethyl, ethoxymethyl or benzyloxymethyl.

The ditertiary diphosphines preferably conform to the formula $$X_1—R^{11}—X_2 \quad\quad (IX)$$

wherein $X_1$ and $X_2$ have the significances given above and $R^{11}$ signifies unsubstituted $C_{2-4}$-alkylene or $C_{2-4}$-alkylene substituted with $C_{1-6}$-alkyl, $C_{1-6}$-alkoxy, $C_5$- or $C_6$-cycloalkyl, phenyl, naphthyl or benzyl; 1,2- or 1,3-cycloalkylene, 1,2- or 1,3-cycloalkenylene, 1,2- or 1,3-bicycloalkylene or 1, 2 or 1,3-bicycloalkenylene, each with 4 to 10 carbon atoms and either unsubstituted or substituted with $C_{1-6}$-alkyl, phenyl or benzyl; 1,2- or 1,3-cycloalkylene, 1,2- or 1,3-cycloalkenylene, 1,2- or 1,3-bicycloalkylene or 1,2- or 1,3-bicycloalkenylene, each with 4 to 10 carbon atoms and being augmented at its 1- and/or 2-position or at its 3-position with bound methylene or $C_{2-4}$-alkylidene; 1,4-butylene substituted at the 2- and 3-positions with —O—CR$_b$R$_c$—O— and being either unsubstituted at its 1- and/or 4-position or substituted at such position(s) with $C_{1-6}$-alkyl, phenyl or benzyl, and wherein each of R$_b$ and R$_c$ independently, signifies hydrogen, $C_{1-6}$-alkyl, phenyl or benzyl, 3,4- or 2,4-pyrrolidinylene or methylene-4-pyrrolidin-4-yl of which in each case the nitrogen atom is substituted or unsubstituted with $C_{1-12}$-alkyl, phenyl, benzyl, $C_{1-12}$-alkoxycarbonyl, $C_{1-8}$-acyl or $C_{1-12}$-alkylaminocarbonyl; or 1,2-phenylene, 2-benzylene, 1,2-xylylene, 1,8-naphthylene, 1,1'-dinaphthylene or 1,1'-diphenylene, each unsubstituted or substituted with halogen, hydroxyl, $C_{1-6}$-alkyl, $C_{1-6}$-alkoxy, phenyl, benzyl, phenoxy or benzyloxy; or a group of one of the following formulae

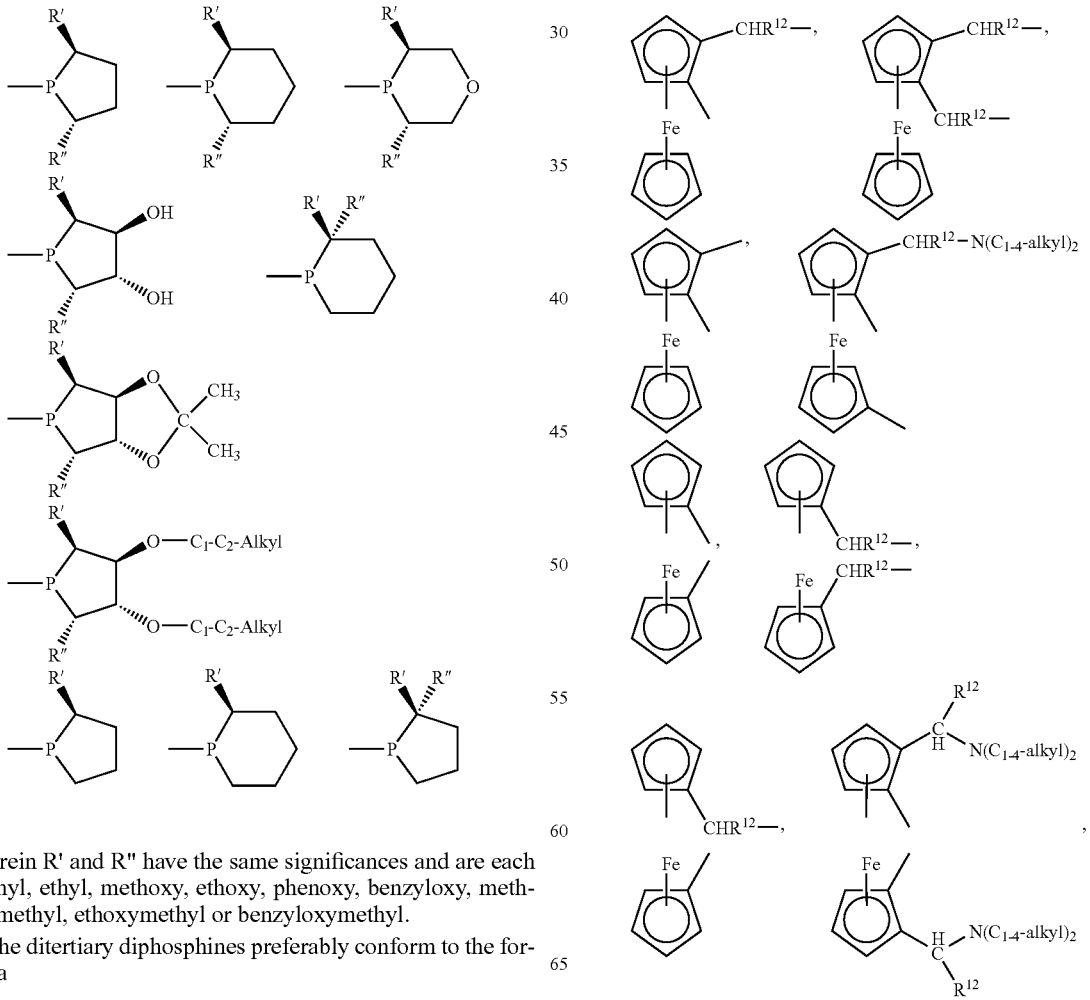

-continued

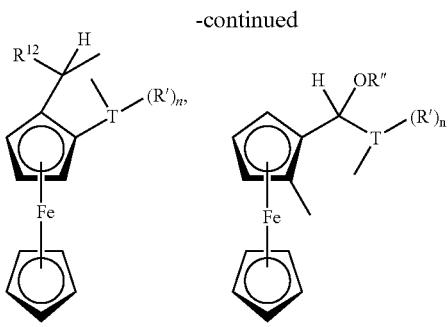

in which $R^{12}$ signifies hydrogen, $C_{1-8}$-alkyl, $C_{1-4}$-fluoroalkyl, unsubstituted phenyl or phenyl bearing up to 3 substitutents the same or different, selected from fluorine, chlorine, bromine, $C_{1-4}$-alkyl, $C_{1-4}$-alkoxy and fluoromethyl;

n signifies 0 or an integer 1 to 4 and R' or each R', independently, signifies $C_{1-4}$-alkyl, $C_{1-4}$-fluoroalkyl or $C_{1-4}$-alkoxy;

T signifies $C_{6-20}$-arylene or $C_{3-16}$-heteroarylene;

the free bond is located in the ortho position to T-cyclopentadienyl;

R" signifies hydrogen, $R_{001}R_{002}R_{003}Si-$, $C_{1-18}$-acyl substituted with halogen, hydroxyl, $C_{1-8}$-alkoxy; $R_{004}R_{005}N-$ or $R_{006}-X_{001}C(O)-$;

each of $R_{001}$, $R_{002}$ and $R_{003}$, independently, signifies $C_{1-12}$-alkyl, unsubstituted $C_{6-10}$-aryl or $C_{7-12}$-arylalkyl or such a group substituted with $C_{1-4}$-alkyl or $C_{1-4}$-alkoxy;

each of $R_{004}$ and $R_{005}$, independently, signifies hydrogen, $C_{1-12}$-alkyl, $C_{3-8}$-cycloalkyl, $C_{6-10}$-aryl or $C_{7-12}$-aralkyl, or $R_{004}$ and $R_{005}$ together form trimethylene, tetramethylene, pentamethylene or 3-oxapentylene;

$R_{006}$ signifies $C_{1-18}$-alkyl; $C_{3-8}$-cycloalkyl unsubstituted or substituted with $C_{1-4}$-alkyl or $C_{1-4}$-alkoxy; $C_{6-10}$-aryl or $C_{7-12}$-aralkyl, and $X_{001}$ signifies $-O-$ or $-NH-$.

The cyclopentadienyl rings in the above formulae can, each, independently, be substituted, e.g. with $C_{1-4}$-alkyl. The tertiarly monophosphine and the ditertiary diphosphines can be used in the form of racemates or mixtures of diastereoisomers or they can be used in essentially enantiomeric pure form.

A preferred group of achiral and chiral diphosphines are those of the formulae X to XXIX:

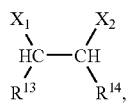 (X)

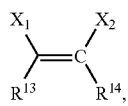 (XI)

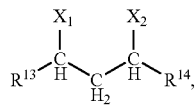 (XII)

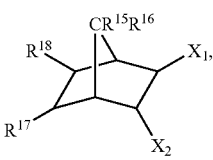 (XII)

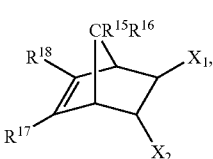 (XIV)

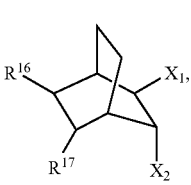 (XV)

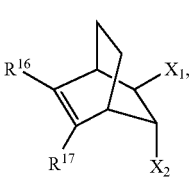 (XVI)

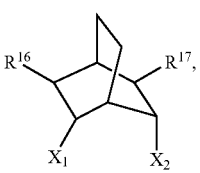 (XVII)

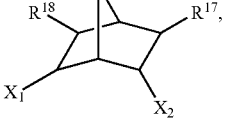 (XVIII)

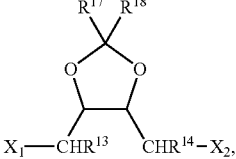 (IXX)

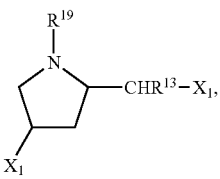 (XX)

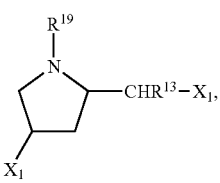 (XX)

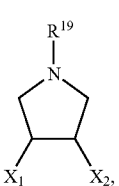 (XXI)

-continued

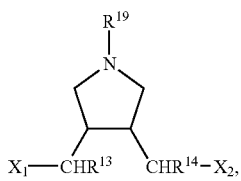

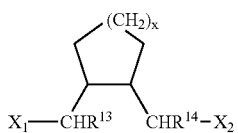

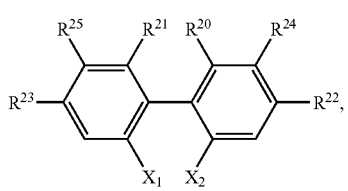

(XXIV)

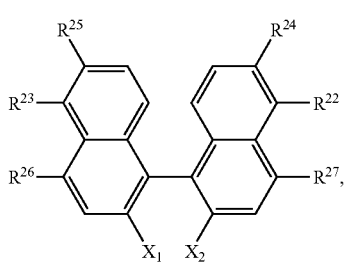

(XXV)

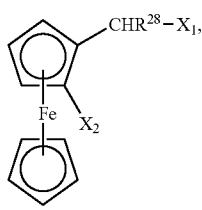

(XXVI)

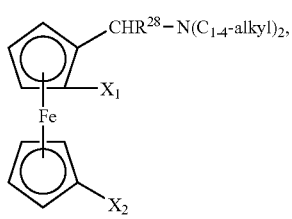

(XXVII)

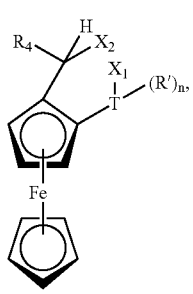

(XVIII)

-continued

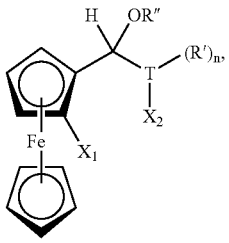

(XXIX)

wherein $R^4$, T, R', R", $X_1$ and $X_2$ have the significances given above, including the preferred significances, $R^{13}$ and $R^{14}$, each independently, signify hydrogen, $C_{1-4}$-alkyl, phenyl or benzyl, the latter two groups being unsubstituted or (aromatically) substituted with 1 to 3 $C_{1-4}$-alkyl and/or $C_{1-4}$-alkoxy groups, $R^{15}$ and $R^{16}$, each independently, signify hydrogen, $C_{1-4}$-alkyl, phenyl or benzyl, $R^{17}$ and $R^{18}$, each independently, signify hydrogen, $C_{1-4}$-alkyl, $C_{1-4}$-alkoxy, phenyl or benzyl, the latter two groups being unsubstituted or (aromatically) substituted with 1 to 3 $C_{1-4}$-alkyl and/or $C_{1-4}$-alkoxy groups, $R^{19}$ signifies hydrogen, $C_{1-12}$-alkyl, phenyl, benzyl, the latter two groups being unsubstituted or (aromatically) substituted with 1 to 3 $C_{1-4}$-alkyl and/or $C_{1-4}$-alkoxy groups, $C_{1-12}$-alkoxy-C(O)—, phenyl-C(O)—, benzyl-C(O)—, the latter two groups being unsubstituted or substituted with 1 to 3 $C_{1-4}$-alkyl and/or $C_{1-4}$-alkoxy groups, $C_{1-12}$-alkyl-NH—CO, phenyl —NH—C(O)— or benzyl-NH—C(O)—, the latter two groups being unsubstituted or substituted with 1 to 3 $C_{1-4}$-alkyl and/or $C_{1-4}$-alkoxy groups, X signifies 0, 1 or 2, $R^{20}$ and $R^{21}$, each independently, signify $C_{1-4}$-alkyl or $C_{1-4}$-alkoxy, or $R^{20}$ and $R^{21}$ together form oxadimethylene, $R^{22}$, $R^{23}$, $R^{24}$, $R^{25}$, $R^{26}$ and $R^{27}$ signify, each independently, hydrogen, $C_{1-4}$alkyl, $C_{1-4}$-alkoxy, $C_5$- or $C_6$-cycloalkyl or cycloalkoxy, phenyl, benzyl, phenoxy, benzyloxy, halogen, hydroxyl, —(CH$_2$)$_3$—C(O)—O—C$_{1-4}$-alkyl, —(CH$_2$)$_3$—C(O)—N(C$_{1-4}$-allyl)$_2$ or —N(C$_{1-4}$-alkyl)$_2$, or $R^{22}$ and $R^{24}$, and/or $R^{20}$ and $R^{24}$, and/or $R^{23}$ and $R^{25}$, and/or $R^{21}$ and $R^{25}$, or $R^{24}$ and $R^{26}$ and/or $R^{25}$ and $R^{27}$ each together form a fused 5- or 6-membered mono- or bicyclic hydrocarbon ring, and $R^{28}$ signifies hydrogen, $C_{1-6}$-alkyl, cyclohexyl or phenyl.

Some preferred examples of chiral ditertiary diphosphines are those of the following formulae:

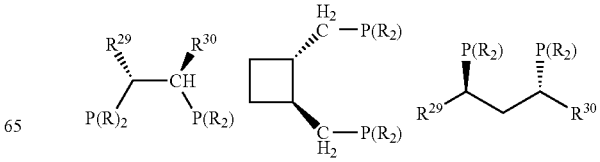

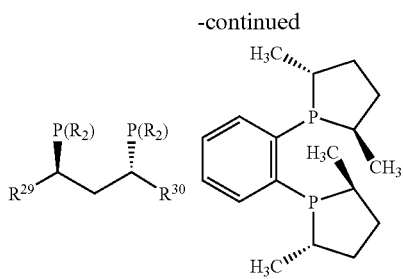
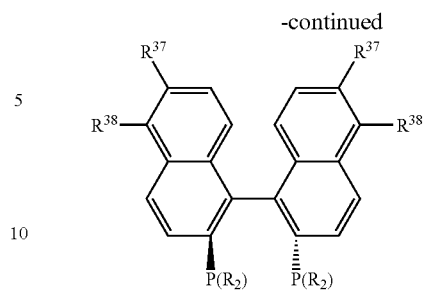

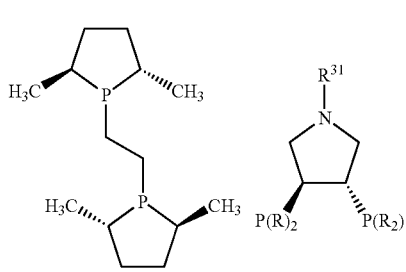
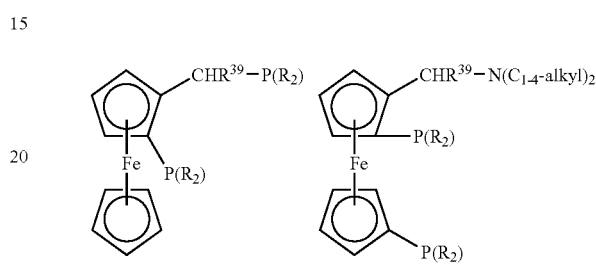

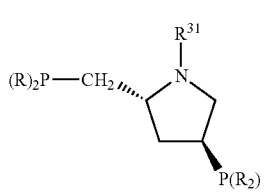
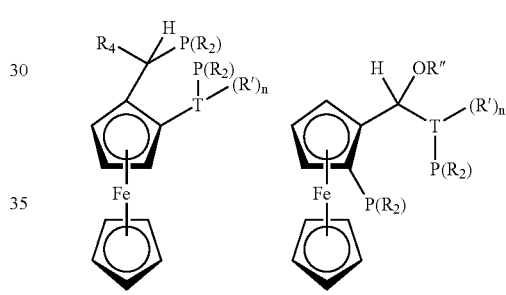

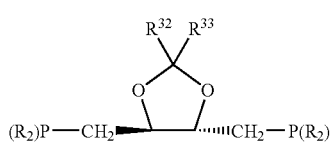

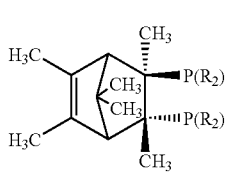

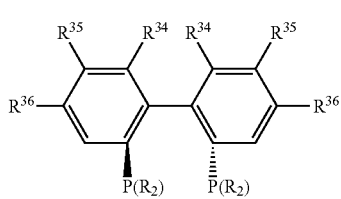

wherein R signifies branched $C_{3-8}$-alkyl, cyclohexyl, norbornyl, adamantly, unsubstituted phenyl or phenyl substituted with 1 to 3 $C_{1-4}$-alkyl, $C_{1-4}$-alkoxy and/or trifluoromethyl groups, or with amino, $(C_{1-4}$-alkyl)NH— or $(C_{1-4}$-alkyl)$_2$N—, $R^4$ signifies hydrogen or $C_{1-4}$-alkyl, T signifies 1,2-phenylene, R' hydrogen and R" $C_{1-4}$-alkyl, $R^{29}$ and $R^{30}$, each independently signify $C_{1-4}$-alkyl, phenyl or benzyl, most preferably methyl, $R^{31}$ signifies $C_{1-8}$-alkyl, $C_{1-8}$-acyl or $C_{1-8}$-alkoxycarbonyl, $R^{32}$ signifies hydrogen or, independently, has the significance of $R^{33}$, and $R^{33}$ signifies $C_{1-4}$-alkyl, phenyl or benzyl, $R^{34}$ signifies methyl, methoxy or both $R^{34}$ together oxadimethylene, $R^{35}$ and $R^{36}$, each independently, signifies hydrogen, $C_{1-4}$-alkyl, $C_{1-4}$-alkoxy or $(C_{1-4}$-alkyl)$_2$N—, $R^{37}$ and $R^{38}$, each independently, signify hydrogen, $C_{1-4}$-alkyl, $C_{1-4}$-alkoxy, —(CH$_2$)$_3$—C(O)—O—$C_{1-4}$-alkyl or —(CH$_2$)$_3$—C(O)—N(C$_{1-4}$-alkyl)$_2$, and $R^{39}$ signifies $C_{1-4}$-alkyl, most preferably methyl.

Suitable ditertiary diphosphines with heterocyclic structures are described in EP-A-0 770 085, by T. Benincori et al. in J. Organomet. Chem. 529 (1997), pages 445-453 and in J. Org. Chem. 61, page 6244 (1996), by F. Bonifacio et al. in Chiratech 1997, 11-13, November 1997, Philadelphia, Pa., USA and by L. F. Tietze et al., Chem. Commun. pages 1811-1812 (1999). Some examples are

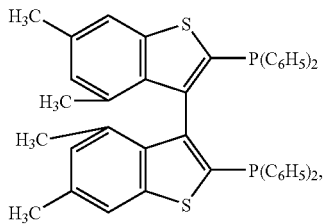

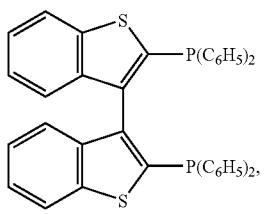

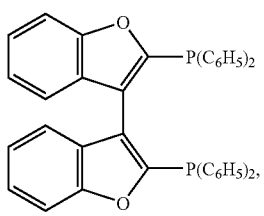

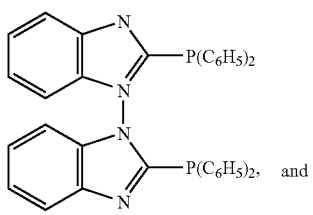

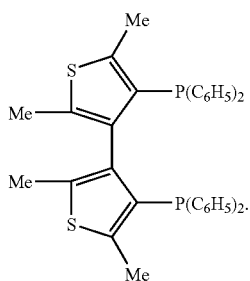

Suitable ditertiary diphosphines are also described for example in Comprehensive Asymmetric Catalysis (E. N. Jacobsen, A. Pfalz and H. Yamamoto (eds.)), Vol. I-III, Springer-Verlag, Berlin, 1999.

As the hydrogen source for the hydrogenation there may be used hydrogen itself or a hydrogen donor, such as an aliphatic alcohol, e.g. isopropanol, or ammonium formate.

The process in accordance with the invention can be effected in an inert solvent, or in the absence of a solvent. Suitable solvents include aliphatic, cycloaliphatic and aromatic hydrocarbons, examples thereof being pentane, hexane, petrol esters, cyclohexane, methylcyclohexane, benzene, toluene and xylene; optionally fluorinated alcohols, examples thereof being methanol, ethanol, propanol, butanol, ethylene glycol monomethlyl ether and diethylene glycol monomethyl and monoethyl ethers (the latter three examples also belonging to the solvent class ethers), and 1,1,1-trifluoroethanol; aliphatic and cyclic ethers, examples thereof being diethyl ether, dibutyl ether, tert. butyl methyl ether, ethylene glycol dimethyl ether, ethylene glycol diethyl ether, diethylene glycol dimethyl ether, tetrahydrofuran, dioxan and diethylene glycol monomethyl and monoethyl ethers (the latter two examples also belonging to the solvent class alcohols); aliphatic ketones, examples thereof being acetone and methyl isobutyl ketone; aliphatic carboxylic acid, e.g. acetic acid; aliphatic carboxylic acid esters and lactones, e.g. methyl acetate, ethyl acetate and valerolactone; aliphatic carboxylic acid amides, e.g. N,N-dimethyl acetamide and dimethylformamide; N-substituted lactones, e.g. N-methylpyrrolidone; cyclic ureas, e.g. N,N-dimethyl-imidazolidin-2-one; aliphatic and alicyclic sulphoxides and sulphones, examples thereof being dimethyl sulphoxide, dimethyl sulphone, tetramethylene sulphoxide and tetramethylene sulphone; and water. The solvent can be used in the process as the sole one, or a mixture of at least two solvents, e.g. taken from the above classes or examples thereof, may be used. Preferred classes of solvents are the hydrocarbons, the alcohols and the ethers.

The metal or the metal constituent of the metal complex catalyst is suitably used in an amount, relative to the amount of cyclic dicarboxylic acid anhydride starting material, in the range from about 0.0001 to about 10 mol %, preferably from about 0.001 to about 10 mol %, and most preferably from about 0.1 to about 5 mol %.

In addition to the employed metal catalyst a co-catalyst can be used in the process in accordance with the invention. Such a co-catalyst is suitably an alkali metal or substituted or unsubstituted ammonium, particularly quaternary ammonium, halide. The alkali metal is particularly lithium, sodium or potassium, and the halide particularly bromide or iodide, preferably the latter. In respect of the quaternary ammonium halide, the substituents on ammonium are suitably lower alkyl, especially $C_{1-6}$-alkyl, groups and/or aryl, especially phenyl, groups. In the case where a co-catalyst is used the amount thereof relative to 1 equivalent of the employed metal catalyst is suitably from about 0.1 to about 100 equivalents, preferably from about 10 to about 80 equivalents.

Moreover, as well as with the co-catalyst, the process of the present invention may also be carried out in the presence of a protonic acid, for example a mineral acid, a carboxylic acid or a sulphonic acid. Examples of such protonic acids are hydrochloric acid, acetic acid and p-toluenesulphonic acid, respectively. If not simultaneously in the role of a solvent for the process, the protonic acid is suitably used in an amount from about from about 0.001 weight percent (wt. %) to about 50 wt. %, preferably from about 0.1 wt. % to about 50 wt. %.

Literature on the simultaneous employment of co-catalysts and protonic acids includes U.S. Pat. Nos. 5,371,256, 5,446,884, 5,583,241 and EP-A-0 691 949.

The process in accordance with the invention is effected at temperatures conveniently from about −20° C. to about 150° C., preferably from about −10° C. to about 100° C., and most preferably from about 10° C. to about 80° C. In general the optical yields achieved are higher when the reaction is performed at lower temperatures in these ranges than at the higher temperatures. On the other hand a more rapid conversion is generally achieved at the higher temperatures than at the lower temperatures.

Moreover, the (hydrogenation) process can be effected under normal or under an elevated pressure. Typically a pressure in the range form about 0.1 MPa to about 20 MPa is employed.

The metal catalyst can be employed in the process in accordance with the invention as such (preformed), or may be formed in situ in the presence of the cyclic dicarboxylic acid anhydride starting material and other materials, e.g. solvent and co-catalyst, involved in the reaction. It can furthermore be advantageous in the case of using a preformed catalyst to augment the reaction mixture with ligand(s), or in the case of an in situ preparation of the catalyst to use an excess of ligand(s); such ligand excess can amount to up to a 6 molar excess, preferably up to 2 molar excess, based on the molar amount of the employed noble metal catalyst.

Depending on the employed catalyst, reaction conditions and solvent (if used) either the lactone of the formula I or the hydroxylactone of the formula I' or the ring-opened hydroxylactone of the formula I" is obtained chemoselectively. The stereoselectivity with which I, I' or I" is obtained also depends on the employed catalyst, reaction conditions and solvent (if used).

In general the process of the present invention can be performed batchwise or continuously.

The process in accordance with the present invention is preferably applied for hydrogenation a cyclic dicarboxylic acid anhydride of the general formula

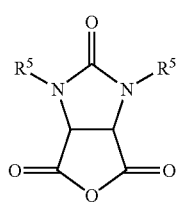

IIa wherein each $R^5$, independently, signifies one of the meanings given above for $R^4$ and $R^5$, preferably hydrogen, substituted or unsubstituted alkenyl, substituted or unsubstituted arylalkyl, heterocyclyl, —COalkyl, —SO$_2$alkyl, —SO$_2$aryl or —Si(alkyl)$_3$, especially allyl, benzyl, p-methoxybenzyl, 1-furyl, 2-furyl, 1-thienyl or 2-thienyl.

in the presence of a metal catalyst to yield the appropriate lactone of the general formula

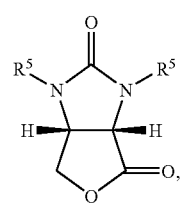

Ia preferably enantioselectively in an optical purity greater than 50% ee (in the 3aS, 6aR form).

The invention is illustrated by the following Examples.

General Procedure for the Hydrogenation of "Biotin Anhydride" (CAN: Formula IIa, Wherein $R^5$=$R^5$=Benzyl)

The following procedure is typical for the hydrogenation experiments (~1 mmol scale). A 50 ml stainless steel autoclave was purged with argon by setting the pressure to 10-12 bar and releasing it. This operation was repeated 4 times. The starting material CAN (0.25 g, 0.74 mmol) and 8 ml of degassed dichloromethane were placed in a 20 ml Schlenck flask with a stirring bar and a sequence high vacuum/argon-filling repeated 6 times. In a second 10 ml Schlenck flask (also under argon, same procedure as above) [Ir(cod)Cl]$_2$ (5.0 mg; 0.0074 mmol) and (S)-xyl-solphos (12.1 mg; 0.0156 mmol) were dissolved in dichloromethane (2 ml). The ratio substrate/Ir was 50. These solutions were stirred at room temperature for 10 minutes and then transferred via canula to the autoclave with a gentle argon flow. The autoclave was purged with hydrogen (10 bar, 4 times), set at 80 bar, the temperature was maintained at 60° C., and stirring started. After 17 hours reaction time, the pressure was released. The reaction mixture was a clear solution. It was evaporated to dryness under reduced pressure. Conversion and chemoselectivity, diastereoselectivity and enantiomeric purity were determined by HPLC. The conversion was >99% and the enantiomeric excess 86.6% (L).

In the procedures various Ru, Rh and Ir catalysts with chiral diphosphine ligands were used as the metal catalysts in the manufacture of the described lactone product of formula Ia, wherein $R^5$=$R^5$=benzyl, with high chemo- and enantioselectivity. The results are presented in the next three tables. The employed ligands and the further symbolized entries are indicated in the legend following the final table and comments.

The results of the asymmetric hydrogenation of CAN with various chiral Ru catalysts under various reaction conditions are compiled in Table 1.

TABLE 1

| Example | Ligand abs. config. | Ligand | Solvent | T °C. | CAN | Lactone | ee | abs. config. | BP1 | CAC | BP2 | RT12.7 |
|---|---|---|---|---|---|---|---|---|---|---|---|---|
| 1 | (R,R') (S,S') | PhTrap | THF | 70 | <0.5 | 77 | 59 | D | 23 | >0.1 | <0.5 | <0.5 |
| 2 | (R)-(S) | (3,5-Me-4-MeOPh)$_2$PF—PtBu$_2$ | DCM | 50 | 12.7 | 2.1 | 57 | D | <0.1 | 14.4 | 50 | 0.5 |
| 3[a] | (S)-(R) | Ph$_2$PPhCHOH-T-PPh$_2$ | Tol/DCM | 80 | 46.3 | 22.2 | 49 | L | <0.1 | 2.3 | 1.1 | 28.1 |
| 4[a] | (S) | Binaphane | DCM | 60 | <0.5 | 52.7 | 16 | L | <0.1 | 6.6 | 8.9 | 7 |
| 5[a] | (R)-(R) | xyl$_2$PPhFc-CH(CH$_3$)Pxyl$_2$ | THF | 70 | <0.5 | 67 | 15 | L | <0.1 | 4 | traces | <0.5 |
| 6[a] | (R) | Xyl-solphos | DCM | 80 | 77.3 | 16.1 | 12 | L | <0.1 | <0.1 | 1.5 | 5.1 |
| 7 | (R)-(S) | MOD-mandyphos | THF | 70 | 0.3 | 20.5 | 12 | D | 2.4 | 12 | 25 | 8 |
| 8 | (R)-(R) | Ph$_2$PPhFc-CH(CH$_3$)—P(3,5-CF$_3$Ph)$_2$ | DCM | 60 | 96 | 0 | — | — | <0.1 | <0.1 | 3.8 | <0.5 |
| 9 | (S) | MeO-biphep | THF | 70 | 78.7 | 0.5 | n.d. | n.d. | <0.1 | 10.2 | 9.8 | <0.1 |
| 10 | (S)-(R) | PPF—PtBu$_2$ | DCM | 50 | 29.4 | 1.6 | n.d. | n.d. | <0.1 | 20.9 | 39.7 | 8.4 |
| 11 | (S)-(R) | PPF—PtBu$_2$ | DCM | 50 | n.d. | n.d. | n.d. | n.d. | <0.1 | n.d. | n.d. | n.d. |
| 12[a] | (S) | MeO-biphep | DCM | 90 | 1.1 | 62.2 | rac | | <0.1 | 27.3 | 2.4 | 6.9 |

Reation conditions: Catalyst: [RuI$_2$(p-cymene)]$_2$ + 1.1 eq. PP; s/c: 50; p(H$_2$): 80 bar; solvent volume 10 ml; time: 15-22 hours
[a] Additive: triethylamine (10 eq/Ru);

Comments:
Using Ru catalysts generated in situ from [RuI$_2$(p-cymene)]$_2$ and a chiral diphosphine (1.05 eq./eq. Ru), d-biotin with up to 59% enantiomeric purity was obtained when CAN was subjected to 80 bar hydrogen at 50-80° C. The best enantioselectivity was observed when (R,R')—(S,S')-PhTrap was used as ligand. Furthermore, with the Ru/PhTrap catalyst both high conversion and a high chemoselectivity were achieved.

Medium enantioselectivities, but incomplete conversions were achieved with the ligand (MeOPh)$_2$PF—PtBu$_2$ (57% ee) and hydroxyl-taniaphos ligand Ph$_2$PPhCHOH-T-PPh$_2$ In the presence of the catalyst Ru/(MeOPh)$_2$PF—PtBu$_2$, only a small fraction of the desired lactone is formed and the main product is the by-product BP2 (Example 2) This result indicates that the first step in the asymmetric hydrogenation of cyclic anhydrides is the formation of a succinaldehydic acid derivative. Subsequently, elimination of water affords the desired lactone. This elimination seems to be rate-determining when Ru/(MeOPh)$_2$PF—PtBu$_2$ is used as catalyst under the described reaction conditions.

The solvents were selected on the basis of solubility data. However, a biphasic reaction mixture is obtained when large amounts of water are formed in presence of the used solvents. Such biphasic reaction conditions might be favourable because of the unwanted hydrolysis of both starting material (CAN) and the Lactone.

The result of the asymmetric hydrogenation of CAN with chiral Rh catalysts are summarized in Table 2.

TABLE 2

| Example | Catalyst | Ligand abs. config. | Ligand | Solvent | T °C. | CAN | Lactone | ee | abs. config. | CAC | BP2 | RT 12.7 |
|---|---|---|---|---|---|---|---|---|---|---|---|---|
| 13 | [Rh]$^+$ | (S)-(R) | PPF—PtBu$_2$ | THF | 50 | 9.4 | 12.3 | 57.5 | L | 8.2 | 70.1 | <0.1 |
| 14 | [Rh]$^+$ | (R)-(S) | (4-CF$_3$Ph)$_2$PF—PtBu$_2$ | THF | 50 | 63.3 | 1.4 | 42 | D | 10.5 | 21.2 | <0.1 |
| 15 | [Rh]$^+$ | (R)-(S) | (3,5-Me-4-MeO-Ph)$_2$PF—PtBu$_2$ | THF | 50 | 2.5 | 15.8 | 40 | D | 1.9 | 36 | 20.1 |
| 16 | [Rh]$^+$ | (R)-(S) | (3,5-Me-4-MeO-Ph)$_2$PF-Pxyl$_2$ | THF | 60 | 79.2 | <0.1 | n.d. | n.d. | 12.6 | 8.1 | <0.1 |
| 17 | [Rh]$^+$ | (R) | Xyl-solphos | THF | 50 | 36.7 | <0.1 | n.d. | n.d. | 15.9 | 47.4 | <0.1 |
| 18 | [Rh]$^+$ | (R)-(S) | MOD-mandyphos | DCM | 70 | 49.55 | 3.4 | n.d. | n.d. | 6.4 | 32 | 1 |
| 19 | [Rh]$^+$ | (S) | iPr-MeO-biphep | 1,2-DCE | 80 | 77.6 | <0.1 | n.d. | n.d. | 5 | 0.5 | 17 |
| 20 | [Rh]$^+$ | (R) | cy-biphemp | 1,2-DCE | 50 | >99.5 | <0.1 | n.d. | n.d. | traces | 0.3 | <0.1 |
| 21 | [Rh]$^+$ | (S) | iPr-MeO-biphep | 1,2-DCE | 50 | >99.5 | <0.1 | n.d. | n.d. | traces | traces | <0.1 |
| 22 | [RhPP]$^+$ | achiral | dipFC | THF | 50 | 5.5 | 59.9 | rac. | — | 1.8 | 22.2 | 3.4 |
| 23 | [Rh]$^+$ | (R,R) | bicp | DCM | 70 | 89.1 | <0.1 | <0.1 | n.d. | 6.9 | <0.1 | 1.1 |
| 24 | [RhPP]$^+$ | (S,S,S,S) | rophos | DCM | 70 | 90.5 | <0.1 | <0.1 | n.d. | 4.2 | <0.1 | 1.2 |
| 25 | [RhPP]$^+$ | (S,S) | bis-P* | DCM | 70 | 89.2 | <0.1 | <0.1 | n.d. | 6.8 | <0.1 | 1.1 |

Reaction conditions: Catalyst: [Rh]$^+$: [Rh(nbd)$_2$]BF$_4$; [RhPP]$^+$: [Rh(cod)(PP)]BF$_4$; p(H$_2$): 80 bar; solvent 10 ml; time: 16-17 hours.

Comments:

In general, BP2 is the predominant product formed when chiral Rh diphosphine catalysts are used, which indicates that the elimination of water affording the product is also rate-determining in the presence of Rh catalysts.

The highest enantioselectivities were obtained with ligands of the josiphos family, yielding the Lactone with up to 57.5% enantiomeric purity (with PPF—PtBu$_2$; Example 13).

In this series, Rh catalysts with highly electron rich diphosphines were mainly used.

When using a Rh catalyst generated in situ from [Rh (nbd)$_2$]BF$_4$ and iPr-MeObiphep, no conversion was observed at 50° C., and at elevated temperatures (80° C.) an unknown by-product (retention time RT: 12.7 min.) is the major product.

The results of the asymmetric hydrogenation of CAN by means of chiral Ir diphosphine catalysts are compiled in Table 3.

TABLE 3

| Example | Ligand abs. config. | Ligand | CAN | Lactone | ee | abs. config. | BP1 | CAC | BP2 | RT 12.7 |
|---|---|---|---|---|---|---|---|---|---|---|
| 26 | (S) | MeO-biphep | <0.5 | 48 | 89.6 | L | 0.2 | 0.8 | 20 | <0.1 |
| 27 | (S) | xyl-solphos | <0.5 | 79.4 | 86.6 | L | 14.7 | traces | traces | traces |
| 28 | (R)-(S) | MOD-mandyphos | <0.5 | 84.1 | 54.3 | L | 6.5 | 6 | 0.4 | <0.1 |
| 29 | (R)-(S) | PPF—PtBu$_2$ | 0.2 | 48 | 35.9 | D | 0.3 | 1.5 | 32 | <0.1 |
| 30 | (R)-(R) | xyl$_2$PPhFc-CH(CH$_3$)Pxyl$_2$ | 5.5 | 30 | 34.5 | L | 0 | 24 | 33.4 | 1 |

Reaction conditions: CAN: 0.25 mg (0.74 mmol); catalyst: [Ir(cod)Cl]$_2$ + 1.05 eq. ligand; s/c: 50; solvent: dichloromethane (DCM): 10 ml; p(H$_2$): 80 bar; T: 60° C.; time: 16-17 hours.

Comments:

Ir catalysts generated in situ from [Ir(cod)Cl]$_2$ and a diphosphine showed high activity in the hydrogenation of CAN. Furthermore, an unprecedented high enantioselectivity of 89.6% could be achieved with MeO-biphep (Example 26).

Lactone with a similar enantiomeric purity (86.6%) was obtained with an analogous Ir-xyl-solphos catalyst, but with higher chemoselectivity than with Ir-MeObiphep.

Medium to high enantioselectivities were achieved also with other ligands, such as the mandyphos derivative MOD-mandyphos (54% ee), the josiphos derivative PPF—PtBu$_2$ (36% ee) and the walphos derivative xyl$_2$PPhFc-CH(CH$_3$)Pxyl$_2$ (34% ee).

Again, the chemoselectivity is also dependent on the catalyst/ligand properties.

Legend

Atropisomeric Ligands

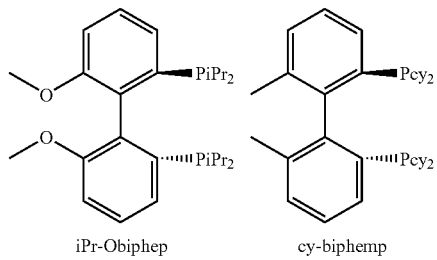

iPr-Obiphep      cy-biphemp

Josphos Ligands

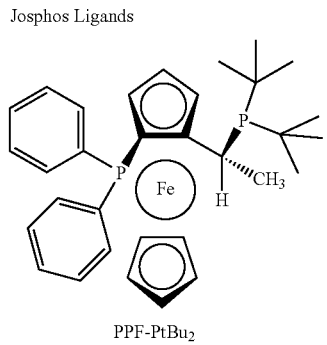

PPF-PtBu$_2$

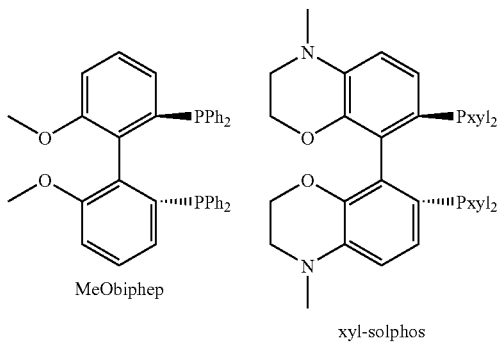

MeObiphep           xyl-solphos

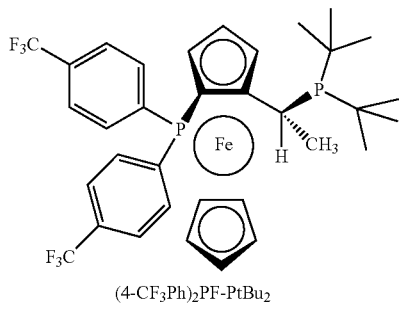

(4-CF$_3$Ph)$_2$PF-PtBu$_2$

-continued
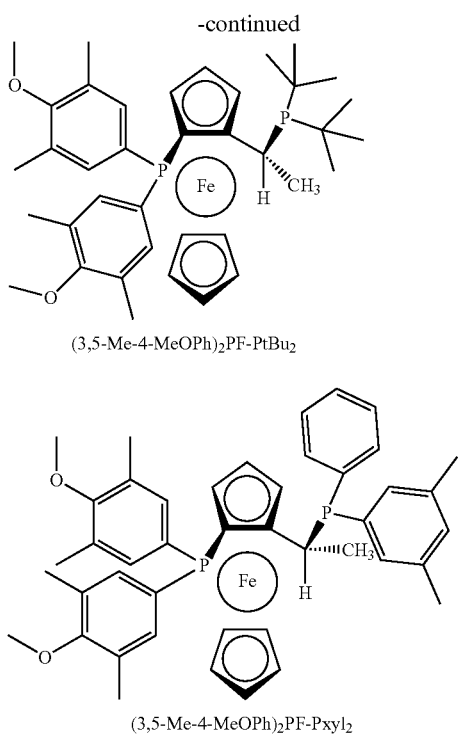
(3,5-Me-4-MeOPh)₂PF-PtBu₂
(3,5-Me-4-MeOPh)₂PF-Pxyl₂
Walphos Ligands
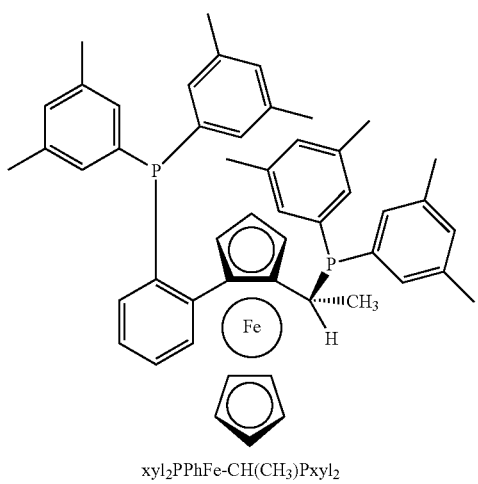
xyl₂PPhFe-CH(CH₃)Pxyl₂
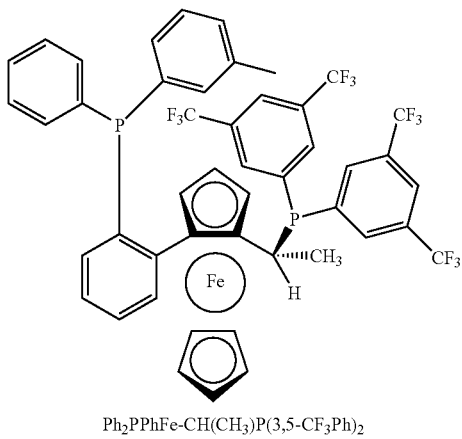
Ph₂PPhFe-CH(CH₃)P(3,5-CF₃Ph)₂
-continued
Other Ligands
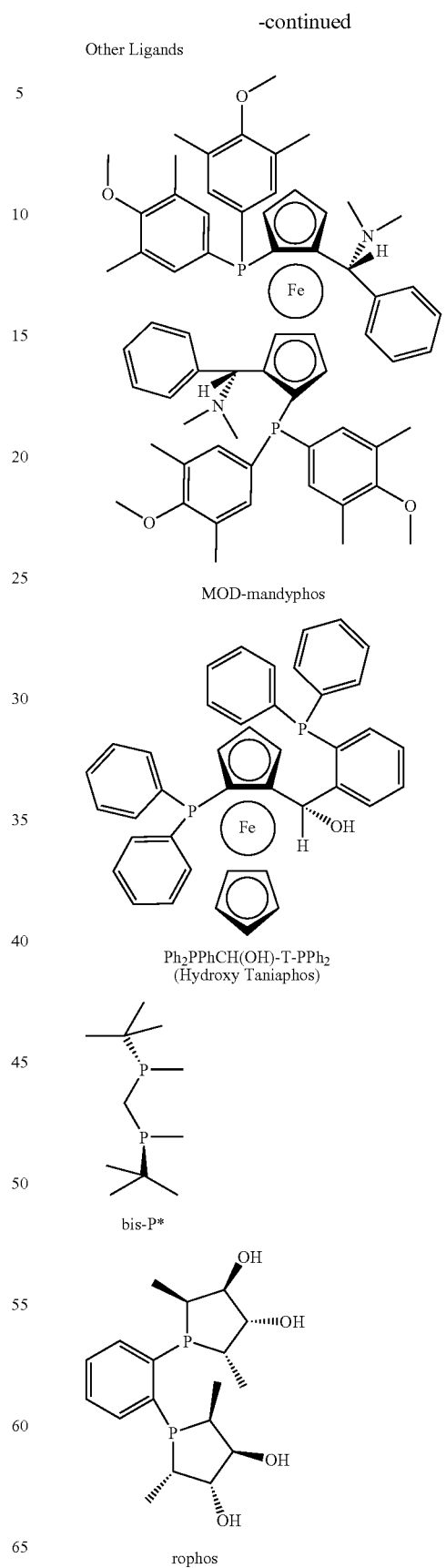
MOD-mandyphos
Ph₂PPhCH(OH)-T-PPh₂
(Hydroxy Taniaphos)
bis-P*
rophos -continued

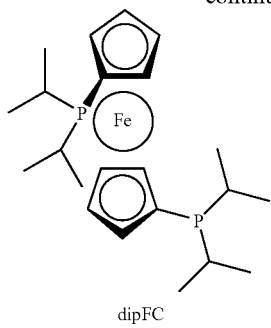

dipFC

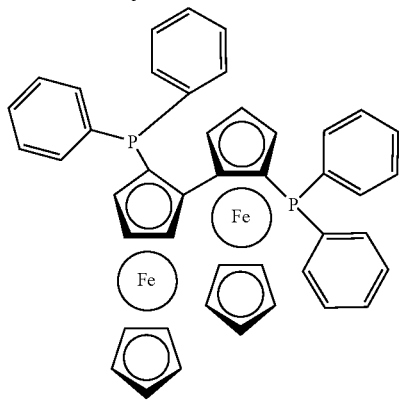

PhTrap

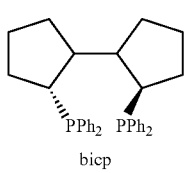

bicp

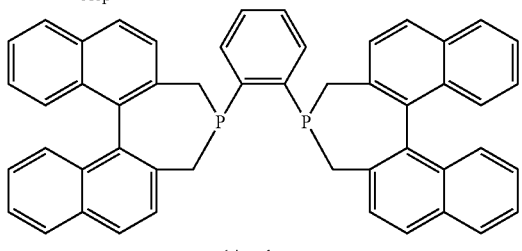

binaphane

CAN: formula IIa, wherein $R^5=R^5=$benzyl
CAC: "ring-opened" CAN, featuring two carboxylic acid groups instead of the anhydride grouping —CO—O—CO—;
Lactone: formula Ia, wherein $R^5=R^5=$benzyl;
BP 1: by-product of formula

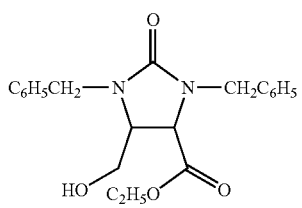

(formed by ethanolysis of the lactone "Lactone")

BP 2: intermediate of the formula I', wherein each of $R^1$ and $R^2$ signify a group (b), the two symbols form together a carbonyl group and each of $R^5$ signify a benzyl group, i.e. the intermediate of the formula

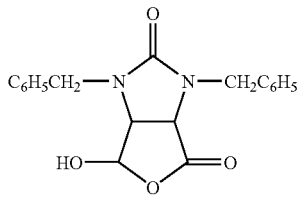

formed in the hydrogenation of CAN;
cod: cyclooctadiene;
nbd: norbornadiene;
PP:
Ph: phenyl;
xyl: 3,5-dimethylphenyl (3,5-xylyl);
iPr: isopropyl;
cy: cyclohexyl;
DCM: dichoromethane;
THF: tetrahydrofuran;
Tol: toluene;
1,2-DCE: 1,2-dichloroethane;
abs. config.: absolute configuration;
ee: enantiomeric purity;
rac.: racemic;
n.d.: not determined;
s/c: substrate (CAN):catalyst ratio;

the figures under Lactone/BP 1/CAC/BP 2/RT 12.7: area percentages as determined by HPLC;
RT: retention time in minutes (CAC: 6.5 minutes; BP 1: 6.0 minutes; BP 2: 9.2 minutes; by-product of unknown structure: 12.7 minutes; designated as "RT 12.7").

The invention claimed is:
1. A process for the manufacture of a lactone of the general formula

Ia

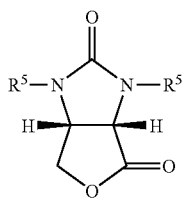

wherein each $R^5$ independently signifies hydrogen, substituted or unsubstituted alkyl, substituted or unsubstituted alkenyl, substituted or unsubstituted cycloalkyl, substituted or unsubstituted aryl, optionally aromatically substituted arylalkyl, optionally aromatically substituted arylalkenyl, cycloalkylalkyl substituted or unsubstituted on the cycloalkyl moiety, heterocyclyl, substituted or unsubstituted alkanoyl, substituted or unsubstituted aroyl, substituted or unsubstituted alkylsulphonyl, substituted or unsubstituted arylsulphonyl or a silyl group Si(alkyl)$_3$, Si(aryl)$_3$ or Si(alkyl)$_{1\ or\ 2}$(aryl)$_{2\ or\ 1}$, and
wherein the process comprises hydrogenating a cyclic dicarboxylic acid anhydride of the general formula:

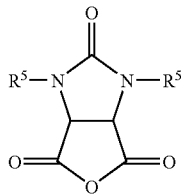

IIa wherein each $R^5$ has the significances given above, in the presence of a group VIII metal catalyst, and wherein the catalyst is chiral and wherein the metal or the metal constituent of the metal complex catalyst is used in an amount, relative to the amount of cyclic dicarboxylic acid anhydride starting material, in the range from about 0.0001 to about 10 mol %.

2. A process according to claim 1, wherein the metal is ruthenium, rhodium or iridium.

3. A process according to claim 1, wherein the catalyst is homogeneous or heterogeneous.

4. A process according to claim 1, wherein the metal catalyst is the metal itself, the metal together with a chiral and/or achiral modifier, or a metal complex comprising a metal and a complexing molecule wherein the metal has formally a zero or positive oxidation state, the metal complex being free or immobilized on a suitable support.

5. A process according to claim 4, wherein the chiral and/or achiral modifier, and/or the complexing molecule, is a mono-, bi- or multidentate compound having one or more phosphorus, nitrogen, oxygen and/or sulphur atoms which act as the linking sites to the metal atom.

6. A process according to claim 1, wherein one or more additional organic compounds with metal-complexing properties and featuring one or more phosphorus, nitrogen and/or sulphur atoms and/or functional groups which can coordinate with the metal are a part of the catalytic system.

7. A process according to claim 1, wherein a homogeneous metal complex catalyst is used which is of formula III or IV

     III

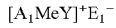     IV wherein $A_1$ signifies two tertiary monophosphine ligands or a ditertiary diphosphine ligand, which together with the metal atom (Me) forms a 5- to 10-membered,
Me signifies a noble metal,
Y signifies two olefines or a diene,
Z signifies Cl, Br or I, and
$E_1^-$ signifies an anion of a protonic or complex acid.

8. A process according to claim 1, wherein the process is effected in a solvent.

9. A process according to claim 1, wherein in addition to the employed metal catalyst a co-catalyst is used which is an alkali metal or a substituted or unsubstituted ammonium halide.

10. A process according to claim 1, wherein the process is carried out in the presence of a protonic acid.

11. A process according to claim 1, wherein the process is effected at temperatures from about −20° C. to about 150° C.

12. A process according to claim 7, wherein $A_1$ together with Me forms a 5-to 8-membered ring.

13. A process according to claim 7, wherein $A_1$ together with Me forms a 5-to 7-membered ring.

14. A process according to claim 7, wherein Me is Rh, Ru or Ir.

15. A process according to claim 8, wherein the solvent is an inert solvent.

16. A process according to claim 15, wherein the solvent is an aliphatic, cycloaliphatic or aromatic hydrocarbon, a fluorinated or unfluorinated alcohol, an open aliphatic or cyclic aliphatic ether, an aliphatic ketone, an aliphatic carboxylic acid, a carboxylic acid ester or lactone, an aliphatic carboxylic acid amide, a N-substituted lactone, a cyclic urea, an aliphatic or alicyclic sulphoxide or sulphone, or water, or a mixtures thereof.

17. A process according to claim 1, wherein the metal complex catalyst is used in an amount relative to the amount of cyclic dicarboxylic acid anhydride starting material, in the range from 0.001 to about 10 mol %.

18. A process according to claim 17, wherein the metal complex catalyst is used in an amount relative to the amount of cyclic dicarboxylic acid anhydride starting material, in the range from 0.1 to about 5 mol %.

19. A process according to claim 9, wherein the co-catalyst is a substituted or unsubstituted quaternary ammonium halide.

20. A process according to claim 10, wherein the protonic acid is a mineral acid, a carboxylic acid or a sulphonic acid.

21. A process according to claim 11, wherein the process is practiced at a temperature from about −10° C., to about 100° C.

22. A process according to claim 21, wherein the process is practiced at a temperature from about 10° C., to about 80° C.

* * * * *